(12) United States Patent
Abou-Saleh et al.

(10) Patent No.: US 6,665,061 B1
(45) Date of Patent: Dec. 16, 2003

(54) METHOD AND DEVICE FOR DETECTING VARIATIONS OF OPTICAL PROPERTIES IN A SAMPLE IN AND ANALYSIS PROCESS

(75) Inventors: Khaled Abou-Saleh, Courbevoie (FR); Patrick Fere, Paris (FR); Alain Rousseau, Paris (FR)

(73) Assignee: Stago International (FR)

( * ) Notice: Subject to any disclaimer, the term of this patent is extended or adjusted under 35 U.S.C. 154(b) by 0 days.

(21) Appl. No.: 09/959,094

(22) PCT Filed: Apr. 21, 2000

(86) PCT No.: PCT/FR00/01070
§ 371 (c)(1),
(2), (4) Date: Oct. 18, 2001

(87) PCT Pub. No.: WO00/65332
PCT Pub. Date: Nov. 2, 2000

(30) Foreign Application Priority Data

Apr. 23, 1999 (FR) .............................................. 99 05226

(51) Int. Cl.⁷ .............................................. G01B 21/00
(52) U.S. Cl. .......................................... 356/73; 356/318
(58) Field of Search ............................ 356/73, 318, 72, 356/39; 250/461.1

(56) References Cited

U.S. PATENT DOCUMENTS

| 4,100,416 A | * | 7/1978 | Hirschfeld | .................. 250/461 |
| 4,284,412 A | * | 8/1981 | Hansen et al. | .............. 250/459 |
| 4,573,796 A | * | 3/1986 | Martin et al. | ............... 356/318 |
| 5,422,720 A | * | 6/1995 | Berndt | ........................ 356/343 |
| 5,489,977 A | * | 2/1996 | Winslow et al. | ............... 356/73 |

* cited by examiner

Primary Examiner—Frank G. Font
Assistant Examiner—Layla Lauchman
(74) Attorney, Agent, or Firm—William A. Drucker

(57) ABSTRACT

The invention concerns a method which consists in performing for a time interval ranging between 1 ms and 10 ms a first turbidimetric measurement using a first light pulse originating from a first source ($SL_1$) emitting in a first frequency range, a second measurement of intensity transmitted in response to a second light pulse originating from a second source ($SL_2$) emitting in a second frequency range and, optionally determining the fluorescence of the sample. The invention is applicable to a biological analysis process as well as to hemostatic analyses.

14 Claims, 3 Drawing Sheets

| Amount of bacteria | small <S− | greater (S− S+) | significant >S+ |
|---|---|---|---|
| LB | −1 | 0 | +1 |
| LV | +1 | 0 | −1 |
| N | −1 | 0 | +1 |
| F | +1 | 0 | −1 |

METHOD AND DEVICE FOR DETECTING VARIATIONS OF OPTICAL PROPERTIES IN A SAMPLE IN AND ANALYSIS PROCESS

BACKGROUND OF THE INVENTION

1. Field of the Invention

The present invention concerns a method and device for detecting the optical properties of a sample, such as a colorimetric variation obtained during a chemical and/or biological analysis process.

It applies in particular to detecting the presence or absence of micro-organisms, such as bacteria or yeast in a sample of a biological material.

2. Description of the Prior Art

In particular, but not exclusively, it is suitable for a detection of this type in a biological analysis process as described in the application WO 96/29427 comprising a separation phase "on gel" consisting of:

- introducing a sample into a centrifugation tube above a gelled system previously introduced into the tube, this system being designed so as to separate the micro-organisms present in the sample according to their size and including a culture medium favouring the development of the micro-organisms and a reactive agent able to induce a detectable optical measurement variation;
- hydro-extract the contents of the tube so as to provoke migration of the micro-organisms present in the sample in the gelled system and promote their development;
- show the presence or absence of the micro-organisms in said system via a detection of said optical measurement variation.

Up until now, this detection has been carried out visually and thus comprised all the drawbacks inherent in this type of detection.

The invention can also be applied in other fields, especially in hemostasis. Thus, it can be used in a method to measure blood coagulation time, as described in the patent U.S. Pat. No. 4,918,984 filed in the name of the Serbio company, and includes a densitometric measurement coupled to a determination of the coagulation time of a blood plasma sample. In this example, these two measurements are obtained with the aid of a device including on both sides of a transparent receptacle the sample firstly a lighting device, and secondly a photodetector in front of which an optical passband filter is placed, this photodetector being connected to an electronic processing circuit.

Subsequently so as to improve this device, the following has in addition been provided:

- firstly a filtering device including several mobile light filters able to be successively brought into the path of the light beam emitted by the incandescent lamp (lighting device), and
- secondly a sampling circuit able to take samples of the measurement signal delivered by the photodetector in synchronism with the running off of the filters and able to associate with each sample an identifier corresponding to the filter used during sampling.

In theory, this solution is able to follow up in real time the variations of the beam detected for each of the wavelength ranges of the filters.

In reality, it does not make it possible to obtain satisfactory results, mainly on account of the run off period of the filters, said period remaining relatively long (without it being able to be reduced) and which results in one sampling in a periodicity of about 2 secs. It is clear that, having regard to this periodicity and the time shift of the detected signals, the comparisons made between these signals becomes dubious and in any event error concerning localisation of the bend remains relatively significant. In addition, owing to the electromechanical portion it introduces, this solution is relatively expensive and requires relatively costly maintenance.

OBJECT OF THE INVENTION

The object of the invention is thus to resolve these problems of slowness and costly mechanical elements and maintenance.

SUMMARY OF THE INVENTION

Thus, the invention concerns a static type method requiring no maintenance and consists of carrying out during a relatively short period of timer of about one millisecond to about ten milliseconds an operational sequence including the following stages:

- a first exposing of the sample to a first incident light pulse whose light waves are included in a first range of frequencies, this pulse being emitted by a first opto-electronic light source,
- a first turbidimetric measurement by a first opto-electronic detector situated approximately in the axis of said incident pulse of the light intensity transmitted from said pulse after passing through said sample,
- the storing of the result of this first measurement in a memory,
- exposing the sample to a second incident light pulse having approximately the same incidence as the first and whose light waves are included in a second range of frequencies, this pulse being emitted by a second opto-electronic light source,
- a second turbidimetric measurement by said first detector of the light intensity of said second pulse after its passage through said sample,
- storing in said memory the result of this second measurement.

Advantageously, the duration of said light pulses could be from one tenth of a millisecond to several milliseconds.

In addition, this method includes, during or after said period, the analysis of the results stored in said memory. Advantageously, said detector shall be of the spectrophotographic type so as to be able to measure the fluorescence of the sample.

This fluorescence measurement could in addition be conjugated with a nephelometric analysis taking into account the optical diffusion properties of the sample.

Thus, in the case when detecting the presence of bacteria, it becomes possible to produce a truth table for exploiting the optical property variations of the sample measured by the detectors and deduce from this an indication of the size of the bacteria population, it being understood that:

- a slightly higher amount of bacteria is expressed by fluorescence,
- an increase of the bacteria generates a reduction of fluorescence, the sample becoming transparent,
- a high amount of bacteria generates a non-transparent and non-fluorescent state able to be detected by the nephelometric measurement.

By means of these arrangements, the various measurements, which are virtually simultaneous (extremely short measuring period) are carried out in the same conditions and thus are extremely reliable. In addition, the interpretation of the measurement results is much more random and false negatives are no longer possible.

BRIEF DESCRIPTION OF THE DRAWINGS

One embodiment of a device for implementing the method of the invention is now described hereafter and given by way of non-restrictive example with reference to the accompanying drawings on which.

DESCRIPTION OF THE PREFERRED EMBODIMENTS

Figure 1:
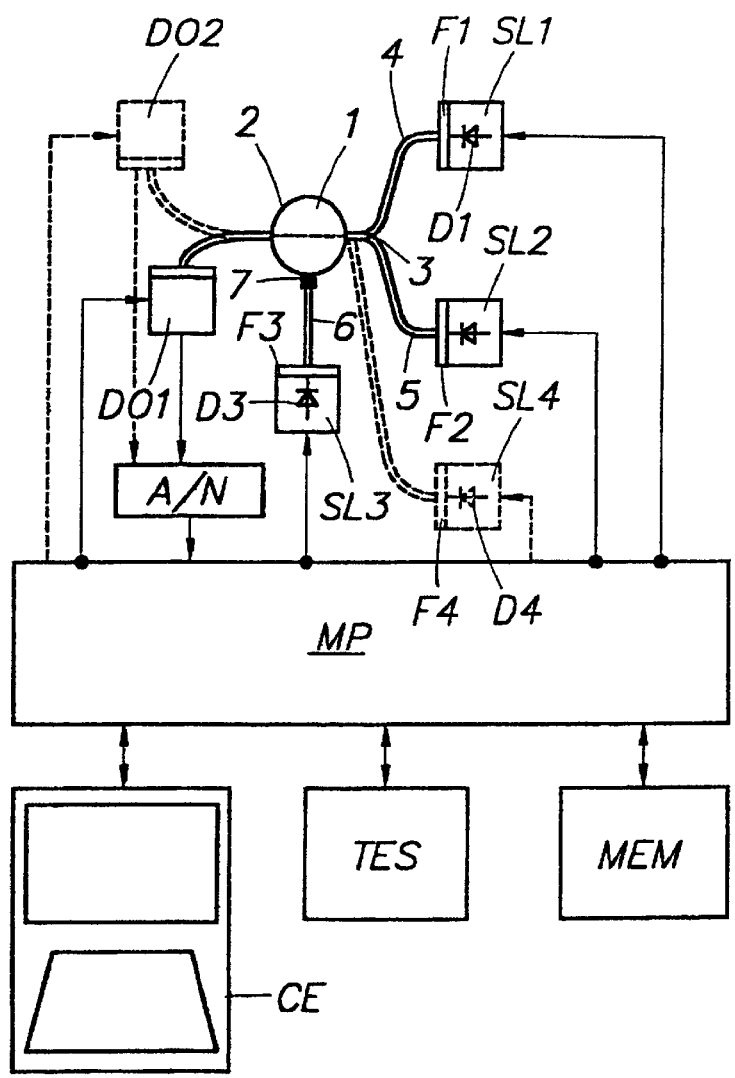
FIG. 1 diagrammatically shows the principle of a device for detecting the variations of the optical properties of a sample in the presence of a reactive agent.

In the example shown on FIGS. 1 to 4, the sample 1 to be analysed is contained in a transparent receptacle 2, for example a test tube, centred perpendicular to the axis of an optical mounting including a system for emitting an incident light beam including firstly at least two light sources $SL_1$, $SL_2$ connected to a transmission head 3 situated close to the tube 2 by means of two respective optical guides 4 and 5 each constituted by an optical fibre, and secondly a third light source $SL_3$ connected by an optical guide 6 to a transmission head 7 centred perpendicular to the axis of the head 3. At least one additional light source $SL_4$ represented by the broken lines could be connected to the transmission head 3 by means of a corresponding wave guide.

The light sources $SL_1$, $SL_2$, $SL_4$ are constituted by luminescent diodes whose light radiation is filtered by filters $F_1$, $F_2$, $F_4$ respectively red (between 600 nm and 700 nm) for the source $SL_1$ and green (between 550 nm and 650 nm) for the source $SL_2$. Similarly, the source $SL_3$ includes a diode $D_3$ and a red filter $F_3$.

The diodes $D_1$ to $D_4$ are controlled by a microprocessor MP so as to transmit successive light pulses of, for example, 2 ms during a measuring period of for example 10 ms.

The device moreover includes at least one detection circuit DO, and in this instance two circuits $DO_1$, $DO_2$ connected to a receiving head 3' by two respective fibres placed in the axis of the transmission head 3 on the side of the tube 2 situated opposite said head 3.

The detectors $DO_1$, $DO_2$ each including a photodiode associated with a filter are controlled by the microprocessor so as to take measurement samples during the emission period of the diodes $D_1$ to $D_4$ and allocate an identifier to them.

The measurement signals produced by the detectors $DO_1$, $DO_2$ are digitised by means of an analog/digital converter A/N before being applied to the microprocessor MP.

Of course, the microprocessor MP is associated with peripheral units, such as a keyboard/screen console CE, an input/output terminal TES for example an RS232 type terminal, and a memory unit MEM.

Figure 2:
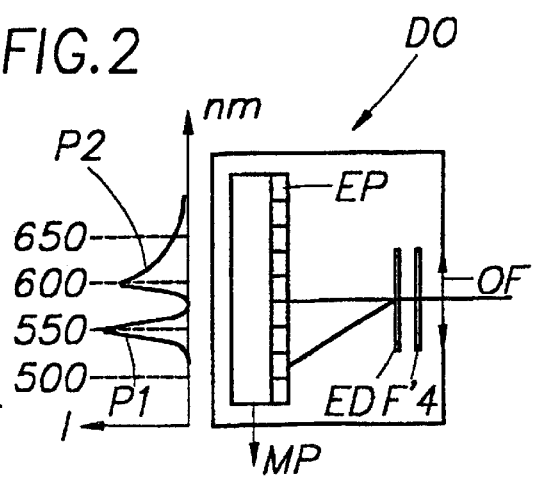
FIG. 2 shows in diagrammatic form the spectrophotometric detector used in the device of FIG. 1.

In the example shown on FIG. 2, the detector DO which can replace the detectors $DO_1$, $DO_2$ of a spectrophotometric detector type. It is composed of a lens OF for projecting ad infinitum the light beam produced by the head 3 or obtained via diffusion of the light produced by the head 7 on a dispersing element ED, such as a prism or a grid by means of a filter $F_4$.

The light dispersed by the element ED is then detected by a bar of photosensitive elements EP, such as a CCD type bar controlled by the microprocessor MP.

By means of this arrangement, it becomes possible to obtain the spectrum of the light transmitted through the sample or diffused by the latter and in addition determine the fluorescence of the sample (which shows a peak whose wavelength is shifted with respect to that of the incident light).

FIG. 2 shows a light intensity diagram according to the wavelength revealing a shift of about 50 nm between an incident light beam derived from the head 3 and transmitted through the sample (peak $P_1$) and the light emitted via fluorescence (peak $P_2$).

The invention is not merely limited to producing such a spectrophotometric detector to measure fluorescence.

In fact, it is possible to carry out a large number of measurements by using suitable combinations of filters associated with the light sources $SL_1$ to $SL_4$ and the detectors $DO_1$, $DO_2$.

Thus, in order to measure fluorescence, it shall be possible to associate with one of the sources $SL_1$, $SL_2$, $SL_4$ for example the source $SL_4$ a low-pass filter $F_4$ which accentuates the green light but does not allow the blue light to pass and to provide a detector, for example the detector $DO_2$, equipped with a high-pass filter which allows the blue light generated by fluorescence to pass.

Figure 3:
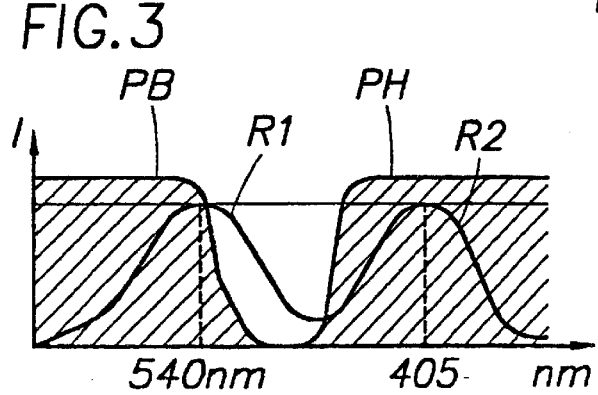
FIG. 3 is a diagram showing the principle of a simplified detection of the fluorescence of the sample.

The diagram shown on FIG. 3 (light intensity I as a function of the wavelength nm) diagrammatically shows:
- the response $R_1$ of the luminescent diode of the source $SL_4$ to an electric pulse,
- the curve of the low-pass filter PB associated with the luminescent diode,
- the light transmitted to the detector $DO_2$ after passing through the sample, the frequency of this light being offset to the blue owing to fluorescence (curve $R_2$),
- the curve of the high-pass filter PH associated with the detector $DO_2$ which allows the blue light generated by fluorescence to pass.

The detector $DO_1$ could then consist of a single photodiode for carrying out the turbidimetric and nephelometric measurements.

Figures 4, 5:
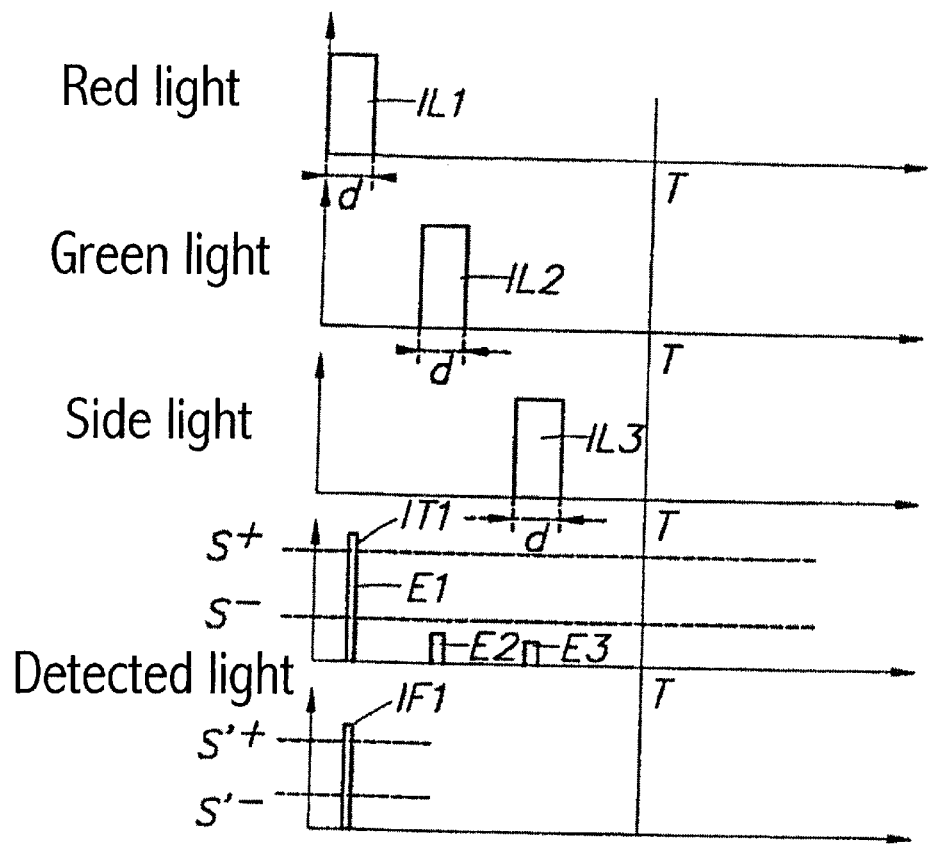
FIG. 4 is a time diagram of a measuring sequence carried out by the device of FIG. 1 in a measuring period.
FIG. 5 is a truth table used to exploit the results of the measurements made by the device.

As mentioned previously, the microprocessor MP controls a succession of measuring sequences each including within an extremely short measuring period T of for example about 10 ms three short duration light pulses d of about 2 ms, the first pulse $IL_1$ being generated by the source $SL_1$, the second pulse $IL_2$ being generated by the source $SL_2$, whereas the third light pulse $IL_3$ is generated by the source $SL_3$ (FIG. 4).

During these three light pulses controlled by the microprocessor MP, the detector DO takes three respective measurement samples, namely:

a first sample $E_1$ from which the following are determined:

the red light intensity $IT_1$ transmitted originating from the source $SL_1$ (wavelength 590 nm), the light intensity $IF_1$ transmitted via fluorescence and whose wavelength is shifted with respect to the incident light by for example a value of 50 nm, a second sample $E_2$ from which the following are determined:

the light intensity IT transmitted derived from the source $SL_2$ for a wavelength of 540 nm, and possibly, the light intensity transmitted by fluorescence, a third sample $E_3$ making it possible to determine the diffused light intensity subsequent to illumination by the source $SL_3$ (nephelometric measurement).

These various measurements make it possible to relatively accurately determine and with no risk of obtaining false negative values the variations of the optical properties and in particular the changing of colour of the sample for example under the effect of the enzymatical secretions of the bacteria on a chromogenic substrate, it being understood that:

when the amount of bacteria is small, a significant fluorescent signal is obtained;

when the amount of bacteria is high, fluorescence reduces, whereas the sample remains transparent;

in the presence of a large amount of bacteria, the sample becomes opaque and diffuses the incident light radiation, this nephelometric signal becoming dominant;

the light intensities detected by the two sources $SL_1$, $SL_2$ both conversely vary according to the colour of the sample and thus the size of the bacteriel population.

FIG. 5 shows a simplified example of a truth table taking into account three logic states of the values measured, namely: state −1 which corresponds to the values measured smaller than a lower threshold S−, a state 0 which corresponds to values measured between the lower threshold S− and an upper threshold S+, and the state +1 which corresponds to values measured greater than the upper threshold S+.

It is clear that on appropriately selecting the thresholds S+ and S−, the detection of the changing of colour of the sample shall be obtained by the simultaneous detection of the values of the parameters LB, LV, N and F moving to 0.

Figure 6:
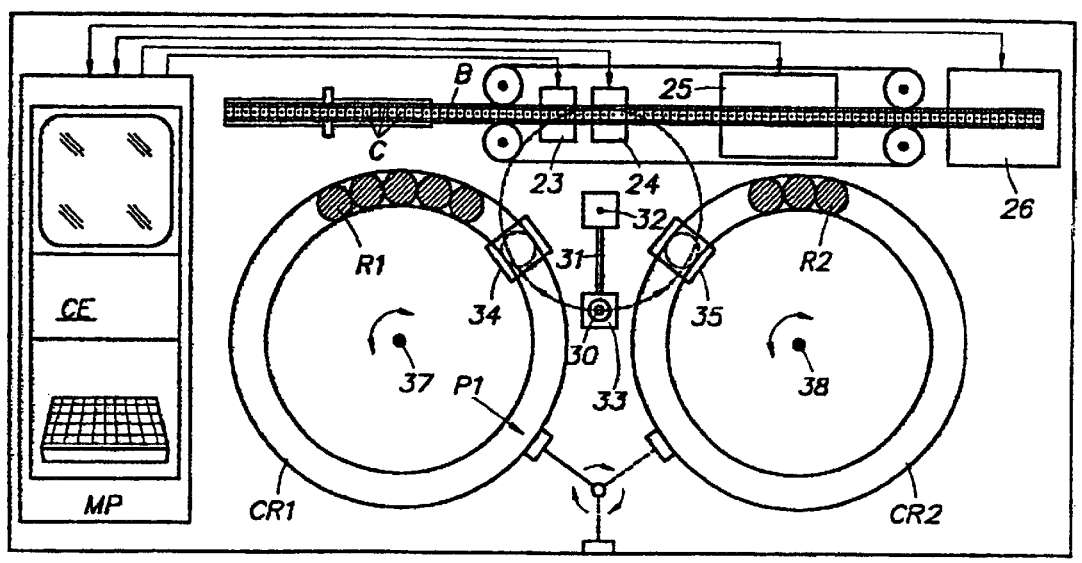
FIG. 6 diagrammatically represents an automatic analysis device using a detection device according to the invention for carrying out biochemical hemostatic analyses.

Advantageously, a device similar to the one previously described could equip an automatic hemostatic analysis device of the type described in the patent application FR No 98 07484 filed on Jun. 10, 1998 in the name of the Applicant and thus a diagrammatic representation is indicated on FIG. 6.

This device introduces a plurality of transparent basins C each intended to contain a liquid sample to be analysed. These basins C are secured to a support strip B successively running off into an incision station 23 of the strip B, a pipette station 24, a detection station 25 equipped with a device of the type shown on FIG. 1, and a recovery station 26 of the strip B fitted with its used basins C.

The pipette station 24 is served by a vertical pipette 30 able to move upwards. This pipette 30 is fixed to one of the extremities of an arm 31 mounted rotating around a vertical spindle 32 so as to be able to be brought by means of rotation successively to the pipette area 24, to a rinsing area 33 and to two sampling areas 34, 35.

The sampling areas 34, 35 are situated in the path of the receptacles $R_1$, $R_2$ borne by two respective carrousels $CR_1$, $CR_2$ able to rotate around two vertical spindles 37, 38 controlled by two servomotors, one of the carrousels $CR_1$ being intended to contain the receptacles $R_1$ with samples, whereas the other $CR_2$ contains receptacles $R_2$ allocated to the reactive agents able to be used in the analyses to be carried out.

The processor P controls pipette sequences including in succession:

a prior rinsing of the pipette 30, the taking of a sample dose contained in one of the receptacles $R_1$ of the carrousel $CR_1$, the injection of this dose into a basin C situated in the pipette station 24, rinsing of the pipette 30, the sampling of a reactive agent dose contained in one of the receptacles $R_2$ of the carrousel $CR_2$, the injection of this reactive agent dose into the basin C, the triggering of at least one sequence of measurements, such as the one previously described, so as to detect a change of colour/or quantitative evaluation of one or several constituents of the sample.

A preliminary feasibility study has shown that the device of the invention obtained excellent results for the rapid localisation of urinal bacteria so as to eliminate a urinary infection and the detection of mycobacteria in the biological samplings.

The tests carried out during this study concerned samples contained in two different types of tubes containing a given substrate and designed to provide a concentration of the micro-organisms of the sample to be tested in a revealing zone having reduced dimensions constituted by a capillary, namely:

SCREEN GEL® mycobact tubes including a capillary in which the mycobacteria is concentrated after agitation via sedimentation with the gel, SCREEN GEL® Uri types including a capillary containing a gel revealing phase in which the micro-organisms penetrate via hydro-extraction.

A) Principle

1) For the SCREEN GEL® mycobact tube, the influence of the gel on the reading made by the device of the invention has been studied by means of a series of tests in a purified system using tubes containing 0.5 ml of a nutrient medium with the gel.

Fluorescence has been read with a pilot production device conforming to the invention, used as a reference device and coupled to a microprocessor which has been programmed to be able to display the result curves on a screen.

These tests have shown that the reading of the change of colour was much easier and more advanced in the presence of gel.

The fluorescence F has been read parallel to the change of colour and it was observed that the increase of fluorescence ($\Delta F$) calculated by the ratio of the fluorescence read at the moment of the change of colour with respect to the start fluorescence (R=Ftx/Ft0) is higher and more advanced in the presence of gel (m$\Delta F$>3.8) that in the absence of gel (m$\Delta F$>2.9) irrespective of the inoculum ($10^6$ and $10^4$ UFC/ml).

2) For the SCREEN GEL® Uri, the concentration of bacteria is ensured by hydro-extraction on the capillary portion of the tube containing the gel phase.

B) Reading Windows

Determination of the reading windows of the two types of tubes has resulted from about a hundred fluorescence, nephelometric and turbidimetric measurements carried out starting from the bottom of the tube up to the top of the capillary.

Figure 7:
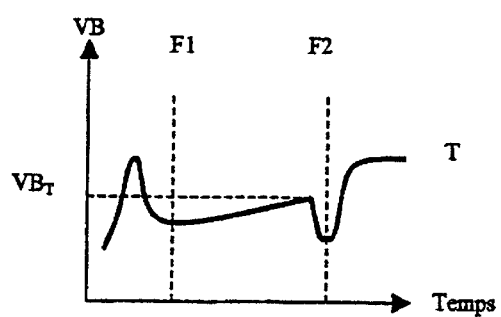
FIGS. 7 and 8 are curves representative of the values detected by a reading device conforming to the invention in the case of SCREEN GEL® Uri tubes (FIG. 7) and SCREEN GEL® mycobact tubes (FIG. 8).

For the SCREEN GEL® Uri tube, the reading windows are delimited by turbidimetry: as shown on, FIG. 7, the bottom of the tube is represented by the first turbidimetric peak; the top of the capillary is represented by the decrease of turbidimetry in the presence of waste matter or by the decrease of fluorescence for the sample/gel interface without waste matter.

For the SCREEN GEL® mycobact tune (FIG. 8), there is no end of reading window as there is no gel/sample interface. The fluorescence and nephelometry values read are therefore maximum irrespective of their localisation.

Figure 8:
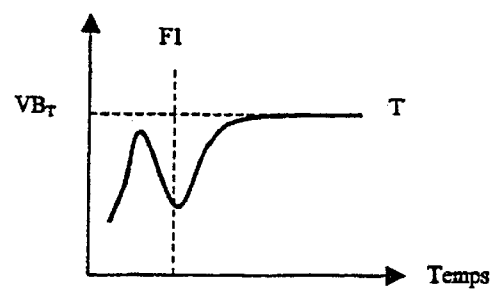

On FIGS. 7 and 8:

VB denotes gross values,

T denotes turbidimetric values

VBT denotes gross turbidimetric values read in the reading window

F1 denotes the start of reading window

F2 denotes the end of reading window.

C) Study in a Purified System

A study in a purified system concerned the evolution of the parameters of the reading device in the presence of mycobacteria.

1) It is observed that turbidimetry does not evolve according to the growth of mycobacteria, irrespective of the inoculum and the substrate concentration.

2) The increase of nephelometry is linked:

to the speed of growth of the phylum: the variation of nephelometry is behind irrespective of the phylums, to the size of the inoculum: the nephelometry variation is much later when the inoculum is slight. There is a delay of four days for the phylum *M.kansasii* at $10^6$ UFC/ml and 8 days for this phylum $10^4$ UFC/ml. The same applies for the phylum *M.tuberculosis* (delay of 6 and 9 days respectively), to the concentration of the substrate: the variation of N is much weaker and behind when the substrate concentration reduces.

For the phylum *M.avium*, this increase appears in 5 days for a substrate concentration of 22.7 mg/l and in 11 days for a concentration of 11.35 mg/l.

It thus appears that the nephelometry increase indicting bacteria multiplication is behind. Thus this parameter has little interest in a purified system.

3) As regards fluorescence, the increase of fluorescence ΔF depends on:

the speed of growth of the phylum: this is proportional to growth;

the inoculum: this is much more advanced and intense when the inoculum is large, the substrate concentration: this is more advanced when the substrate concentration reduces for the phylum of *M.tuberculosis* with a low CMI (CMI 20 mg/l) and for the phylum of *M.kansasii* whose growth is slowed down by the substrate. The optimum concentration of the substrate is 11 mg/l, stability at 37° C. of the test specimen tubes: the increase of F (ΔF) of the test specimen tubes is progressive. The increase of fluorescence of the test tubes needs to be greater that that of the test specimen tubes bred in the same conditions so that the test is positive. So as to simplify reading, we prefer to calculate the fluorescence F ratio (test)/fluorescence (test specimen) rather than calculate the increase of fluorescence with respect to the test tubes and the test specimen tubes.

The test is positive when the ratio is >1.55. It is limited when the ratio is between 1.4 and 1.55 and in this case it is necessary to incubate for a longer period.

Determination of fluorescence is perceptible (ratio of 1.5 to 3.0) and advanced or indeed more advanced than fluorescence of the tube MGIT, especially for the slow growth phylums *M.xenopi* and *M.tuberculosis*.

Determination of fluorescence thus allows an advanced and perceptible detection of the respiratory activity of mycobacteria. The reading on the device makes it possible to reduce the substrate concentration which in particular inhibits the growth of the phylums of *M.tuberculosis*.

D) A System Examination of Overloaded Samplings is Able to Determine the Evolution of the Parameters of the Reading Device in the Absence of Mycobacteria and in the Presence of Mycobacteria.

In the absence of mycobacteria, the following have been observed:

the stability of the substrate at 45° C. and at 37° C. is similar in a samplings system (n=3) and in a purified system, fluorescence progressively increases and in a similar way in a purified system. The ratio F of the sampling test specimen tubes with respect to a test specimen tube is <1.3, nephelometry reflects the presence of waste matter in the samplings.

In the presence of mycobacteria, the fluorescence ration of the overloaded samplings has been determined in tubes containing about 11 mg/l of substrate and taking as a reference a buffer specimen test tube and the same threshold as previously. It is observed that the average detection delays are shorter than in a buffer. Nevertheless, it seems that the presence of waste matter in large quantities delays or marks the appearance of the colour pink and fluorescence, especially for the phylums of *M.tuberculosis*.

Determination of fluorescence by the device thus allows detection of mycobacteria in overloaded samplings in similar delays, the other parameters having no significant interest.

E) Conclusion

In conclusion, the device of the invention can be used for reading SCREEN GEL® mycobact tubes:

by using tubes without hydro-extraction, by reducing the substrate concentration revealing fluorescence. The initially selected concentration to correctly display a change of colour inhibits or delays the growth of the phylums of *M.tuberculosis* in particular.

However, by simplifying the method of detection:

it is not necessary to delimit the reading windows, fluorescence is the only parameter of any interest as a marker of the activity of mycobacteria, the gross fluorescence value indicated is the maximum value read during the path traversed in the capillary and is independent of its localisation in the capillary, detection of fluorescence is sufficient: F linked to the appearance of the colourless non-fluorescent derivative is not destroyed as kinetic reading every day and then every weeks stops upon generation of the fluorescent pink derivative, reading is carried out by taking as a reference a buffer type sample tube incubated in the same conditions as the tubes to be tested. The interpretation of the ratio of the fluorescence of the tubes to be tested on F of the type sample tube makes it possible to mitigate evolution of fluorescence for two months of incubation at 37° C. and thus the instability of the substrate at this temperature, the measurement of fluorescence on the device allows a quantitative and advanced determination of the change of colour and renders the result independent of the operator;

the adjustment of the device is limited to the fluorescence fibre: calibration to the use of positive controls and control on the use of SCREEN GEL® mycobact tubes.

What is claimed is:

1. Method for detecting a variation of the optical properties of a sample to be analysed, said method consisting of carrying out during a relatively short period of time of about one millisecond to about ten milliseconds an operational sequence comprising at least the following stages:
  i. a first exposure of the sample to a first incident light pulse whose light waves are included in a first range of frequencies, this pulse being emitted by a first opto-electronic light source,
  ii. a first turbidimetric measurement by an opto-electronic detector situated approximately in the axis of said first incident pulse of the light intensity transmitted from said first pulse after passing through said sample,
  iii. a storage of the result of this first measurement in a memory,
  iv. an exposure of the sample to a second incident light pulse having approximately the same incidence as first and whose light waves are included in a second frequency range, this pulse being emitted by a second opto-electronic light source,
  v. a second measurement of the intensity transmitted from said second pulse after passing through said sample,
  vi. a storage of the result of this second measurement in said memory,
  vii. an exposure of the sample to a third light pulse emitted by a third opto-electronic light source orientated perpendicular to the said first and second opto-electronic light sources,
  vii a third nephelometric measurement by said detector,
  viii. a storage of the result of the third measurement in said memory,
  ix. an analysis of the results stored in said memory.

2. Method according to claim 1, which comprises a succession of operational sequences and a comparative analysis of the results of these sequences.

3. Method according to claim 1, wherein the duration of said light pulses is about one tenth of a millisecond to ten milliseconds.

4. Method according to claim 1, which further comprises during one of the two first measurements a determination of the fluorescence of the sample.

5. Method according to claim 1, wherein said measurements are carried out with the aid of several detectors, one of these being specifically used to determine fluorescence.

6. Method according to claim 5, wherein the measurement of fluorescence is obtained by the conjugation of filtering one of said incident light pulses by a lowpass filter which accentuates the green light but does not allow the blue light to pass and a filtering of the light transmitted in response to said pulse by a highpass filter which allows the blue light generated by fluorescence to pass.

7. Method according to claim 1, wherein the third pulse is orientated perpendicular to the other two and that the measurements are carried out by a given detector.

8. Method according to claim 7, wherein said measurements are spectrophotometric measurements.

9. Method according to claim 1, wherein the analysis of the results is made with the aid a previously memorised truth table.

10. Device for detecting a variation of the optical properties of a sample to be analysed, said device comprising:
  i. a first opto-electronic light source emitting in a first wavelength range a light beam applied by means of a first optical guide to a transmission head axed towards a transparent receptacle containing a sample to be analysed,
     a second light source emitting inside a second wavelength range a light beam applied to said transmission head,
  ii. at least one third light source connected by means of a third optical guide to a transmission head centered on the transparent receptacle perpendicular to the axis of said first transmission head,
     at least one opto-electronic detector placed in said axis at a location situated on the side of the receptacle situated opposite said transmission head so as to give an information about an intensity of said first light bean after passing through said sample,
  a microprocessor comprising:
    i. means for controlling said first opto-electronic light source so as to expose said sample to a first incident light pulse whose light waves are included in a first range of frequencies,
    ii. means for storing the turbidimetric measurement provided by said opto-electronic detector in response to said first incident light pulse,
    iii. means for controlling said second opto-electronic light source so as to expose said sample to a second incident light pulse having approximately the same incidence as the first and whose light waves are included in a second frequency range,
    iv. means for storing the second measurement provided by said opto-electronic detector in response to said second incident light pulse,
    v. means for controlling said third opto-electronic light source so as to expose said sample to a third light pulse,
    vi. means for storing the third nephelometric measurement provided by said opto-electronic detector in response to said third incident light pulse,
    vii. an analysis of the results stored in said memory.

11. Device according to claim 10, wherein the light sources each comprise a luminescent diode and an optical filter.

12. Device according to claim 10, wherein said detector is a spectrophotometric detector.

13. Device according to one of claims 10, which comprises a third light source connected by means of a third optical guide to a transmission head centered on the transparent receptacle perpendicular to the axis of said first head, this third light source being used to carry out a nephelometric measurement and being controlled by said processor.

14. Device according to one of claims 10, which is integrated in the measuring station of an automatic analysis device introducing a plurality of transparent basins intended to each contain a liquid sample to be analysed, these basins being secured to a support strip successively running off in an incision station of the strip, a pipette station, said measuring station and a recovery station of the strip provided with its used basins.

* * * * *